(12) United States Patent
Burzynski (10) Patent No.: US 12,186,290 B2
(45) Date of Patent: *Jan. 7, 2025

(54) METHODS FOR THE TREATMENT OF GLIOBLASTOMA MULTIFORME

(71) Applicant: Stanislaw R. Burzynski, Houston, TX (US)

(72) Inventor: Stanislaw R. Burzynski, Houston, TX (US)

(*) Notice: Subject to any disclaimer, the term of this patent is extended or adjusted under 35 U.S.C. 154(b) by 177 days.

This patent is subject to a terminal disclaimer.

(21) Appl. No.: 17/587,197

(22) Filed: Jan. 28, 2022

(65) Prior Publication Data

US 2022/0151968 A1 May 19, 2022

Related U.S. Application Data

(60) Division of application No. 16/843,850, filed on Apr. 8, 2020, now Pat. No. 11,234,951, which is a continuation of application No. 15/589,887, filed on May 8, 2017, now Pat. No. 10,624,869.

(51) Int. Cl.
| | |
|---|---|
| A61K 31/198 | (2006.01) |
| A61K 31/192 | (2006.01) |
| A61K 31/197 | (2006.01) |
| A61K 31/436 | (2006.01) |
| A61K 31/44 | (2006.01) |
| A61K 31/506 | (2006.01) |
| A61K 39/395 | (2006.01) |
| A61K 45/06 | (2006.01) |
| A61P 35/00 | (2006.01) |
| C07K 16/22 | (2006.01) |
| A61K 39/00 | (2006.01) |

(52) U.S. Cl.
CPC .......... *A61K 31/198* (2013.01); *A61K 31/192* (2013.01); *A61K 31/197* (2013.01); *A61K 31/436* (2013.01); *A61K 31/44* (2013.01); *A61K 31/506* (2013.01); *A61K 39/3955* (2013.01); *A61K 45/06* (2013.01); *A61P 35/00* (2018.01); *C07K 16/22* (2013.01); *A61K 2039/545* (2013.01); *A61K 2300/00* (2013.01)

(58) Field of Classification Search
CPC ..... A61P 35/00; A61K 31/192; A61K 31/197; A61K 31/198; A61K 31/436; A61K 31/506
See application file for complete search history.

(56) References Cited

U.S. PATENT DOCUMENTS

| | | |
|---|---|---|
| 6,258,849 B1 | 7/2001 | Burzynski |
| 10,624,869 B2 | 4/2020 | Burzynski |
| 11,234,951 B2 | 2/2022 | Burzynski |
| 11,334,521 B2 | 5/2022 | Danilov et al. |
| 11,607,397 B2 | 3/2023 | Burzynski |
| 2002/0103141 A1 | 8/2002 | McKearn et al. |
| 2008/0274909 A1 | 11/2008 | Brothman |
| 2016/0158186 A1 | 6/2016 | Brown et al. |
| 2018/0318421 A1 | 11/2018 | Burzynski |

FOREIGN PATENT DOCUMENTS

| | | |
|---|---|---|
| JP | 2002503209 A | 1/2002 |
| WO | WO 97/42939 A1 | 11/1997 |
| WO | WO 2016/128146 | 8/2016 |
| WO | 2018208697 | 11/2018 |
| WO | 2018231733 | 12/2018 |

OTHER PUBLICATIONS

International Search Report and Written Opinion mailed Jul. 18, 2018, 10 pages, from the International Searching Authority, for the corresponding International Application No. PCT/US18/31456.
Cecil Textbook of Medicine, 20th Edition, vol. 1, 1996.
Gura et al. (Science 1997).
Johnson et al., (British J. of Cancer 2001).
Burzynski, Journal of Cancer Therapy, 2014, 5, 1423-1437.
Remington, The Science and Practice of Pharmacy, Nineteenth Edition—1995, p. 710-712.
Burzynski et al., Journal of Cancer Therapy, 2014, 5, 946-956.
Siegelin et al., Neuroscience Letters, 2010, 165-170.
Verhaak et al., Cancer Cell, 2010 17(1); 98.
The Extended Search Report mailed Feb. 24, 2021, 7 pages, from the corresponding European Application No. 18797766.5.
Burzynski S R et al: "Initial Clinical Study With Antineoplaston A2 Injections in Cancer Patients With Five Years' Follow-Up", Drugs Under Experimental and Clinical Research, Bioscience Ediprint Inc, CH, vol. XIII, No. SUPPL. 01,Jan. 1, 1987 (Jan. 1, 1987), pp. 1-12, XP008000446, ISSN: 0378-6501.
Valeriote F et al: "Synergistic Interaction of Anticancer Agents: a Cellular Perspective", Cancer Chemotherapy Reports, XX, XX, vol. 59, No. 5, Sep. 1, 1975 (Sep. 1, 1975), pp. 895-900, XP009019750.
Ma Daniel J. et al: "A phase II trial of everolimus, temozolomide, and radiotherapy in patients with newly diagnosed glioblastoma: Ncctg N057K", Neuro-Oncology, vol. 17, No. 9, Sep. 1, 2015 (Sep. 1, 2015), pp. 1261-1269, XP055776395, US ISSN: 1522-8517, DOI: 10.1093/neuonc/nou328.
Burzynski SR, et al. (2015) Comprehensive genomic profiling of recurrent classic glioblastoma in a patient surviving eleven years following antineoplaston therapy. Cancer Clin Oncol. 4(2):41-52.
Burzynski SR, et al. (1987). Initial clinical study with antineoplaston A2 injections in cancer patients with five years' follow-up. Drugs Exp Clin Res. 13:1-11.

(Continued)

*Primary Examiner* — Shobha Kantamneni
(74) *Attorney, Agent, or Firm* — Polsinelli PC (57) ABSTRACT

Methods for the treatment of cancer, including glioblastoma multiforme (GBM) and recurrent glioblastoma multiforme (RGBM). The method includes administering to a patient a plurality of extraneous antineoplastons and a plurality of targeted agents. The plurality of extraneous antineoplastons may include two or more antineoplastons selected from phenylacetylglutaminate sodium (PG), phenylacetylisoglutaminate sodium (iso-PG), and phenylacetate (PN). The plurality of targeted agents may include two or more agents selected from bevacizumab, pazopanib, sorafenib, dasatinib, and everolimus.

13 Claims, 3 Drawing Sheets

(56) References Cited

OTHER PUBLICATIONS

Burzynski SR, et al. (2014) A phase II study of antineoplastons A10 and AS2-1 in children with high-grade glioma. Final Report (Protocol BT-06), and review of recent trials. J Cancer Therapy. 5:565-577.

Burzynski S, et al. (2022) Newly-Diagnosed Multicentric Pilocytic Astrocytoma: Complete Response and> 22 Years Survival in a Six Year and Nine-month-old Female Treated with Antineoplastons. Internat J Clin Oncol Cancer Res. 7:76-82.

Burzynski SR, et al. (2014) The response and survival of children with recurrent diffuse intrinsic pontine glioma based on phase II study of antineoplastons A10 and AS2-1 in patients with brainstem glioma. Child's Nervous System. 30:2051-2061.

Burzynski SR, et al. (2014). A phase II study of antineoplastons A10 and AS2-1 in children with recurrent, refractory or progressive primary brain tumors—Final report (Protocol BT-22). J Cancer Therapy. 5:977-988.

Burzynski SR, et al. (2021) Long-term survival (27.7 years) following IV Antineoplaston Therapy (ANP) in a 36-year-old-female with a progressive diffuse intrinsic pontine glioma (DIPG). Int J Radiol Imaging Technol. 7:073-078.

Burzynski SR, et al. (2015) A phase II study of antineoplastons A10 and AS2-1 in patients with brainstem gliomas. The report on non-diffuse intrinsic pontine glioma (Protocol BT-11). J Cancer Therapy. 6(4):334-344.

Burzynski SR, et al. (2015) A phase II study of antineoplastons A10 and AS2-1 in adult patients with newly-diagnosed anaplastic astrocytoma. Final report (Protocol BT-08). Cancer Clinical Oncology. 4:28-38.

Burzynski SR, et al. (2015) A Phase II Study of Antineoplastons A10 and AS2-1 in Adult Patients with Primary Brain Tumors—Final Report (Protocol BT-09). J Cancer Therapy. 6:1063-1074.

Ceja ME, et al. (2013). Dosing considerations in pediatric oncology. US Pharm. 38:8-11.

Burzynski SR, et al. (2015). A Phase II Study of Antineoplastons A10 and AS2-1 Injections in Adult Patients with Recurrent Anaplastic Astrocytoma—Final Report (Protocol BT-15). Cancer Clinical Oncology. 4:13-23.

Burzynski SR, et al. (2016) Primary CNS tumors and leptomeningeal, disseminated and/or multicentric disease in children treated in Phase II studies with Antineoplastons A10 and AS2-1. Cancer Clin Oncol. 5.2:38-48.

Burzynski SR, et al. (2016). A Phase II Study of Antineoplastons A10 and AS2-1 in Children with Low-Grade Astrocytomas—Final Report (Protocol BT-13). J Cancer Therapy. 7(12):837-850.

Burzynski SR, et al. (2017). A Phase II study of Antineoplastons A10 and AS2-1 in children with brain tumors. Final Report (Protocol BT-10). J Cancer Therapy. 8(02):173-187.

Burzynski SR, et al. (2017). Antineoplastons A10 and AS2-1 in the treatment of children with optic pathway glioma: Final report for protocol BT-23. Cancer Clin Oncol. 6(1):25-35.

Burzynski SR, et al. (2004) Phase II Study of Antineoplaston A10 and AS2-1 in Children with Recurrent and Progressive Multicentric Glioma: A Preliminary Report. Drugs in R&D. 5(6):315-326.

Burzynski SR, et al. (2021) Long-term survival (23 years) in a 26-year-old male after Antineoplaston therapy for a progressive, diffuse intrinsic pontine glioma: A case report. Int J Brain Disord Treat. 6:038-044.

Burzynski B, et al. (2023) Inoperable Optic Pathway Glioma: A Seven-Year-Old Male with >35 Years Overall Survival Following Treatment with Antineoplastons. European J Clin Med. ISSN:2736-5476.

Johnson JI, et al. (2001). Relationships between drug activity in NCI preclinical in vitro and in vivo models and early clinical trials. British J Cancer. 84(10): 1424-1431.

Burzynski SR, et al. (2022) A 25-year-female with Diffuse Intrinsic Pontine Glioma Surviving for More than Nine Years Following Treatment with Antineoplastons. Cancer Res. 7(1):1-7.

Moon JH, et al. (2012) Leptomeningeal Dissemination of a Low-Grade Brainstem Glioma without Local Recurrence. J Korean Neurosurg Soc. 51(2):109-112.

Reinert T, et al. (2019) Analysis of Plasma Cell-Free DNA by Ultradeep Sequencing in Patients With Stages I to III Colorectal Cancer. JAMA Oncol. 5(8): 1124-1131.

Burzynski S, et al. (2022) Recurrent/Persistent Glioblastoma Complete Response and 24 Years Disease-Free-Survival in a 45-Year-Old Female Treated with Antineoplastons. Cancer Stud Ther J. 7(3):1-6.

Burzynski S, et al. (2022) Recurrent and progressive ganglioglioma in an 11-year-old male treated with antineoplastons: Partial response with more than nine years and nine months survival and complete resolution of clinical symptoms/signs. Biomed Res. 37:1-3.

Burzynski B, et al. (2023) Persistent pineoblastoma: Complete response and >26 years overall survival in a ten-month-old female treated with antineoplastons. Biomed Res Clin Practice. 7:1-5.

Extended European Search Report mailed Jan. 25, 2021 for EP Application No. 18818116.8 (6 pages).

Burzynski SR, et al. (2021) Resolution of clinical signs, a complete response, and long-term survival (> 23 Years) in a 3 and ½ month female with a newly diagnosed diffuse intrinsic pontine glioma treated with antineoplastons. Biomed Res. 6:1-6.

International Search Report and Written Opinion mailed Sep. 7, 2018 for Int'l. Application No. PCT/US18/036972 (7 pages).

Burzynski SR, et al. (2014) A case of sustained objective response of recurrent/progressive diffuse intrinsic pontine glioma with phenylbutyrate and targeted agents. J Cancer Ther. 6(1):40-44.

Burzynski SR, et al. (2011) Successful Treatment of Recurrent Triple-Negative Breast Cancer with Combination of Targeted Therapies. J Cancer Ther. 2:372-376.

Burzynski SR, et al. (2015) Long-term survival (over 20 years), complete response and normal childhood development in medulloblastoma treated with Antineoplastons A10 and AS2-1. J Neurol Stroke. 2(3):00054.

Burzynski SR, et al. (2015) Long-term survival over 21 years and pathologically confirmed complete response in pediatric anaplastic astrocytoma: a case report. J Neurol Stroke. 2(6):00072.

Burzynski SR, et al. (2014) Long-term survival (> 13 years) in a child with recurrent diffuse pontine gliosarcoma: a case report. J Pediatric Hematol Oncol. 36(7):e433.

Burzynski S, et al. (2023) Newly Diagnosed Anaplastic Astrocytoma:> 23 Year Survival in a 31-Year and 11-Month-Old Female Treated with Antineoplastons. Neurol Neurosci. 4(2): 1-6.

Burzynski B, et al. (2022) Twenty-two Year Survival in 15-Year-Old Female with a Recurrent Posterior Fossa Ependymoma Treated with Antineoplastons. Oncol Clin Res. 3(1):99-105.

Burzynski SR, et al. (2015) Complete response and Long-term survival (> 20 years) of a child with tectal glioma: A case report. Pediatric Neurosurgery. 50(2):99-103.

Burzynski S, et al. (2021) Diffuse Intrinsic Pontine Glioma in an 11-Year-Old Female Treated with Antineoplastons: Complete Response and > 25 Years Survival. Pediatrics Neonatal Med. 1(2): 1-5.

Burzynski S, et al. (2022) Newly Diagnosed Glioblastoma: Partial Response and >27 Years Overall Survival in 37-Year-Old Male Treated with Antineoplastons (Treatment of Glioblastoma with Antineoplastons). Recent Adv Clin Trials. 2(2):1-7.

Decision on Rejection for Chinese Patent Application No. 201880045821.3, mailed on Jun. 30, 2023, 6 pages.

Decision to Grant for Japanese Patent Application No. 2019-561860, mailed on Oct. 11, 2022, 3 pages.

Examination Report No. 1 for Australian Patent Application No. 2018266375, mailed on Mar. 29, 2023, 4 pages.

Final Office Action for U.S. Appl. No. 15/589,887, mailed on Dec. 9, 2019, 6 pages.

Final Office Action for U.S. Appl. No. 15/589,887, mailed on Feb. 5, 2019, 17 pages.

Final Office Action for U.S. Appl. No. 16/843,850, mailed on Jun. 23, 2021, 22 pages.

First Office Action for Chinese Patent Application No. 201880045821.3, dated Jul. 13, 2022, 3 pages.

First Office Action for Indonesian Patent Application No. P00201911489, mailed Nov. 10, 2021, 3 pages.

(56) References Cited

OTHER PUBLICATIONS

First Office Action for Israel Patent Application No. IL270543, mailed Mar. 23, 2022, 3 pages.
First Office Action for Mexican Patent Application No. MX20190013345, mailed Mar. 28, 2022, 6 pages (English Translation Provided).
Non-Final Office Action for U.S. Appl. No. 15/589,887, mailed on Jul. 24, 2018, 21 pages.
Non-Final Office Action for U.S. Appl. No. 15/589,887, mailed on Jun. 26, 2019, 23 pages.
Non-Final Office Action for U.S. Appl. No. 16/843,850, mailed on Dec. 9, 2020, 16 pages.
Notice of Allowance for U.S. Appl. No. 15/589,887, mailed on Feb. 12, 2020, 7 pages.
Notice of Allowance for U.S. Appl. No. 16/843,850, mailed on Sep. 24, 2021, 8 pages.
Office Action for Australian Patent Application No. 2018266375, mailed on Oct. 5, 2023, 4 Pages.
Office Action for Canadian Application No. 3,062,741, mailed on Dec. 19, 2023, 6 pages.
Office Action for Japanese Patent Application No. 2019-561860, mailed on Apr. 12, 2022, 4 pages.
Notice of Allowance Mexican Patent Application No. MX20190013345, mailed Oct. 17, 2022, 2 pages.
Search Report for Malaysian Patent Application No. MY2019PI06545, mailed Nov. 9, 2022, 1 page.
Second Office Action for Chinese Patent Application No. 201880045821.3, dated Feb. 5, 2023, 8 pages.
Second Office Action for Indonesian Patent Application No. P00201911489, mailed Mar. 13, 2024, 3 pages.
Second Office Action for Israel Patent Application No. IL270543, mailed Jul. 26, 2023, 4 pages (English Translation Provided).
Second Office Action for Mexican Patent Application No. MX20190013345, mailed Aug. 8, 2022, 3 pages (English Translation Provided).

METHODS FOR THE TREATMENT OF GLIOBLASTOMA MULTIFORME

CROSS REFERENCE TO RELATED APPLICATIONS

This application is a divisional of U.S. Ser. No. 16/843,850, filed Apr. 8, 2000, which is a continuation application of U.S. Ser. No. 15/589,887, filed May 8, 2017, now U.S. Pat. No. 10,624,869, of which the full disclosures of these applications are incorporated herein by reference for all purposes.

FIELD OF TECHNOLOGY

The present disclosure is directed to methods of treating cancer. The present disclosure is further directed to methods for the treatment of glioblastoma and recurrent glioblastoma using antineoplastons and targeted agents.

BACKGROUND

Glioblastoma multiforme (GBM) represents the most frequently occurring and among the most aggressive form of primary malignant brain tumors, accounting for 54% of glioma. A sub-analysis in an international randomized trial by the European Organization for Research and Treatment of Cancer (EORTC) and the National Cancer Institute of Canada (NCIC) compared the results of radiation therapy (RT) alone with those of concomitant RT and temozolomide (TMZ) and found that the addition of TMZ to RT for newly diagnosed GBM resulted in a significant survival benefit. A significant survival benefit of TMZ administration was also found in the subgroup analysis of the 5-year survival data of the EORTC/NCIC trial. Since then, TMZ has been the first-line chemotherapeutic agent for GBM. However, despite aggressive treatment including surgery, radiation therapy (RT), and adjuvant TMZ-based chemotherapy, the prognosis of patients with GBM has been extremely poor, with a median survival of 14.6 months from diagnosis. The median progression-free-survival (PFS) after standard therapy is 6-9 months, demonstrating that current treatment options are palliative rather than curative.

The Cancer Genome Atlas Network has cataloged recurrent genomic abnormalities in GBM. The Network described a gene expression-based molecular classification of GBM into Proneural, Neural, Classical, and Mesenchymal subtypes and integrated multidimensional genomic data to establish patterns of somatic mutations and DNA copy number. Aberrations and gene expression of EGFR, NF1, PDGFRA/IDH1, and EGFR/neuron markers were used to define the Classical, Mesenchymal, Proneural, and Neural subtypes, respectively. The response of GBM to therapy has been found to differ by subtype.

The prognosis for recurrent glioblastoma (RGBM) is much worse than for GBM, with a majority of patients dying within six months. In general, treatment of RGBM may involve repeated resection, focal RT, chemotherapy or experimental therapies. However, there has been very modest progress in the treatment of RGBM and there are no standard treatment recommendations for RGBM. In view of the unfavorable survival outlook with currently available treatment modalities, new methods for the treatment for GBM and RGBM are desirable.

BRIEF DESCRIPTION OF THE DRAWINGS

Embodiments of the present application are described, by way of example only, with reference to the attached Figures, wherein.

It should be understood that the various aspects are not limited to the depictions provided in the drawings.

DETAILED DESCRIPTION

Various embodiments of the disclosure are discussed in detail below. While specific implementations are discussed, it should be understood that this is done for illustration purposes only. A person skilled in the relevant art will recognize that other procedures and techniques can be used without parting from the spirit and scope of the present disclosure.

It should be understood at the outset that although illustrative implementations of one or more embodiments are illustrated below, the disclosed methods can be implemented using any number of techniques. The disclosure should in no way be limited to the illustrative implementations, drawings, and techniques disclosed herein, but can be modified within the scope of the appended claims along with their full scope of equivalents. In addition, numerous specific details are set forth in order to provide a thorough understanding of the embodiments described herein. However, it will be understood by those of ordinary skill in the art that the embodiments described herein can be practiced without these specific details. In other instances, methods, procedures and techniques have not been described in detail so as not to obscure the related relevant feature being described.

The following definitions are provided in order to aid those skilled in the art in understanding the present disclosure. As used herein, the term "objective response" refers to a response of a tumor to a therapeutic treatment. In at least some instances, the term "objective response" refers to a measured reduction in tumor size. In other instances, the term "objective response" can also refer a stopping or arresting of the growth of the tumor. As used herein, the term "concurrently" as in "concurrent administration," in all its forms and uses, refers to the overlapping administration of one or more therapeutic compositions or agents on the same day during at least a portion of its therapeutic regimen. Therefore, for example, the daily intravenous administration of a therapeutic agent administered on at least one overlapping day that a second therapeutic composition is administered orally would represent concurrent administration. Further, a therapeutic composition administered intravenously once every two weeks is concurrently administered with a therapeutic composition that is orally administered daily if the intravenous administration occurs on the same day as at least one day that the oral administration occurs. As used herein, the term "antineoplaston (ANP) therapy," refers to administration to a patient, by any administration route, of an "ANP therapeutic composition" comprising a therapeutically effective amount of Atengenal (A10), Astugenal (AS2-1), or any combination thereof.

The present disclosure provides methods for treating cancer in a patient. According to at least one aspect of the present disclosure, the method includes administering to a patient a plurality of extraneous antineoplastons and a plurality of targeted agents. The plurality of targeted agents may include pazopanib, sorafenib, dasatinib, everolimus, and bevacizumab. The plurality of extraneous antineoplastons may include phenylacetate (PN), phenylacetylglutaminate sodium (PG), phenylacetylisoglutaminate sodium (iso-PG), and any combination thereof. In at least some instances, the cancer may be glioma. In other instances, the cancer may be glioblastoma multiforme (GBM) or recurrent glioblastoma multiforme (RGBM).

In at least some instances, the presently disclosed methods may be used to treat a patient that has failed treatment with surgery, radiation therapy and/or chemotherapy prior to administration of the plurality of extraneous antineoplastons and the plurality of targeted agents. For instance, the presently disclosed method may include treating a patient that has previously failed to achieve an objective response following administration of chemotherapy with temozolomide (TMZ) and/or bevacizumab (BVZ). In some instances, the presently disclosed methods may be used to treat a patient that has previously undergone a resection of a glioma prior to administration of the plurality of extraneous antineoplastons and the plurality of targeted agents. According to at least one aspect of the present disclosure, the method may further include genomic profiling of a tumor in the patient to determine the genetic subtype. In at least some instances, the method may include treating GBM or RGBM in a patient in which the GBM or RGBM is of the Classical or Proneural subtype.

Antineoplastons (ANP) are peptides, amino acid derivatives and carboxylic acids which were initially isolated from the blood and urine of healthy subjects. Because ANP were found to be deficient in the blood of cancer patients, it was postulated that they may have anticancer activity. Antineoplastic activity of these compounds has been shown in a number of clinical and preclinical studies. ANP may be administered to a patient in the form of an ANP therapeutic composition that includes Atengenal (A10), Astugenal (AS2-1), or any combination thereof.

Atengenal (A10) comprises a 4:1 ratio of synthetic phenylacetylglutaminate sodium (PG) and phenylacetylisoglutaminate sodium (iso-PG). PG has a molecular weight of 286.26 and an empirical formula of $C_{13}H_{15}N_2NaO_4$. PG was first described by Thierfelder and Sherwin and is synthesized by the reaction of phenylacetyl chloride with L-glutamine in an aqueous solution containing sodium bicarbonate. PG is a hygroscopic white powder having a melting point of approximately 102° C. and is very soluble in water. The structural formula of PG is:

Iso-PG has a molecular weight of 286.26 and an empirical formula of $C_{13}H_{15}N_2NaO_4$. Iso-PG is synthesized by the reaction of phenylacetyl chloride with L-glutamine in an aqueous solution containing sodium bicarbonate to afford PG, which in turn is heated under vacuum at 160° C. to yield A10C (3-phenylacetylamino-2,6-piperidinedione). When A10C is treated with sodium hydroxide, it produces a mixture of PG and iso-PG in a 4:1 ratio. Iso-PG is a white powder having a melting point of approximately 175-176° C. and is soluble in water. The structural formula of iso-PG is:

Astugenal (AS2-1) comprises phenylacetate (PN) and PG in a 4:1 ratio. PN is characterized by a molecular weight of 158.63 and an empirical formula of $C_8H_8NaO_2$. PN is synthesized by refluxing benzyl cyanide with dilute sulfuric acid or hydrochloric acid. In solid form, PN has a melting point of approximately 76.5° C. The structural formula of PN is:

In at least some instances, ANP therapeutic compositions may be administered to a patient intravenously using, for instance, a dual-channel infusion pump and central venous catheter. In some cases, intravenous administration of ANP therapeutic compositions may occur once every four hours at the infusion rate of from about 50 mL/hr to about 250 mL/hr depending on patient's age and condition/tolerance, in an outpatient setting. AS2-1 or A10 can be administered separately in combination with targeted agents. In such cases, a single channel pump can be used. They can also be administered every 5, 6, or 8 hours.

A published study evaluated the safety and efficacy of ANP therapy in recurrent high-grade glioma, with a special emphasis on RGBM. Burzynski et al. (2014) A phase II study of antineoplastons A10 and AS2-1 in adult patients with recurrent glioblastoma multiforme: Final report (protocol BT-21). *J. Cancer Ther* 5:946-956. In twenty-four patients with RGBM who received at least four weeks of ANP therapy, four patients (16.7%) achieved an objective response while overall survival was 39.3% at one year and 4.4% at two, five, and ten years. A group of RGBM patients with unusually long survival following ANP therapy were identified. Burzynski et al. (2014) Recurrent glioblastoma multiforme—A strategy for long-term survival. *J Cancer Ther.* 5:957-976. Tumor tissue from one of these patients, who was alive and free of disease 11 years after ANP therapy for RGBM, was collected for gene expression profiling. Burzynski et al. (2015) Comprehensive genomic profiling of recurrent classic glioblastoma in a patient surviving eleven years following antineoplaston therapy. *Cancer Clin. Oncol.* 4(2):41-52. In December 2014, comprehensive genomic profiling of the patient tumor tissue was performed by Foundation Medicine, Inc. of Cambridge, MA, using a Next Generation Sequencing (NGS) assay of 343 cancer-related genes and introns. Based on the NGS assay, the patient's RGBM was classified as the Classical subtype. The response of GBM to ANP therapy has been found to differ by subtype, with the greatest benefit being seen in the Classical and Proneural subtypes, which generally responds the least of all the subtypes to standard therapy.

Published data indicate that only some GBM patients will respond to ANP therapy when administered alone. Burzynski et al. (2014) Recurrent glioblastoma multiforme—A strategy for long-term survival. *J. Cancer Ther.* 5:957-976. While PG and PN affect over 100 abnormal genes in the GBM genome, their effect, taken alone, may not be sufficient to consistently alter the GBM genome (~650 abnormal genes) and produce an objective response. Therefore, the present disclosure provides methods for the treatment of cancer, including GBM and RGBM, that includes a combination of therapeutic agents.

RGBM patients have been treated with a combination of sodium phenylbutyrate (PB) and additional targeted agents in conjunction with genomic profiling. Burzynski et al. (2014) Preliminary findings on the Use of Targeted Therapy with Pazopanib and Other Agents in Combination with Sodium Phenylbutyrate in the Treatment of Glioblastoma Multiform. *J. Cancer Ther.* 5:1423-1437. Based on this treatment approach, objective response rates and overall survival exceeded the previously published results in RGBM. Burzynski et al. (2014) *J. Cancer Ther* 5:946-956. Eleven RGBM patients treated with PB in combination with bevacizumab, dasatinib, pazopanib, and m-TOR inhibitors resulted in six patients (54.5%) achieving an objective response and three patients maintaining stable disease (27.3%), providing for an overall disease control rate of 81.8%. The most effective therapeutic regime consisted of PB, bevacizumab, dasatinib, everolimus and pazopanib. All patients who complied with this treatment regime achieved an objective response. Burzynski et al. (2014) *J. Cancer Ther.* 5:1423-1437.

Figure 1:
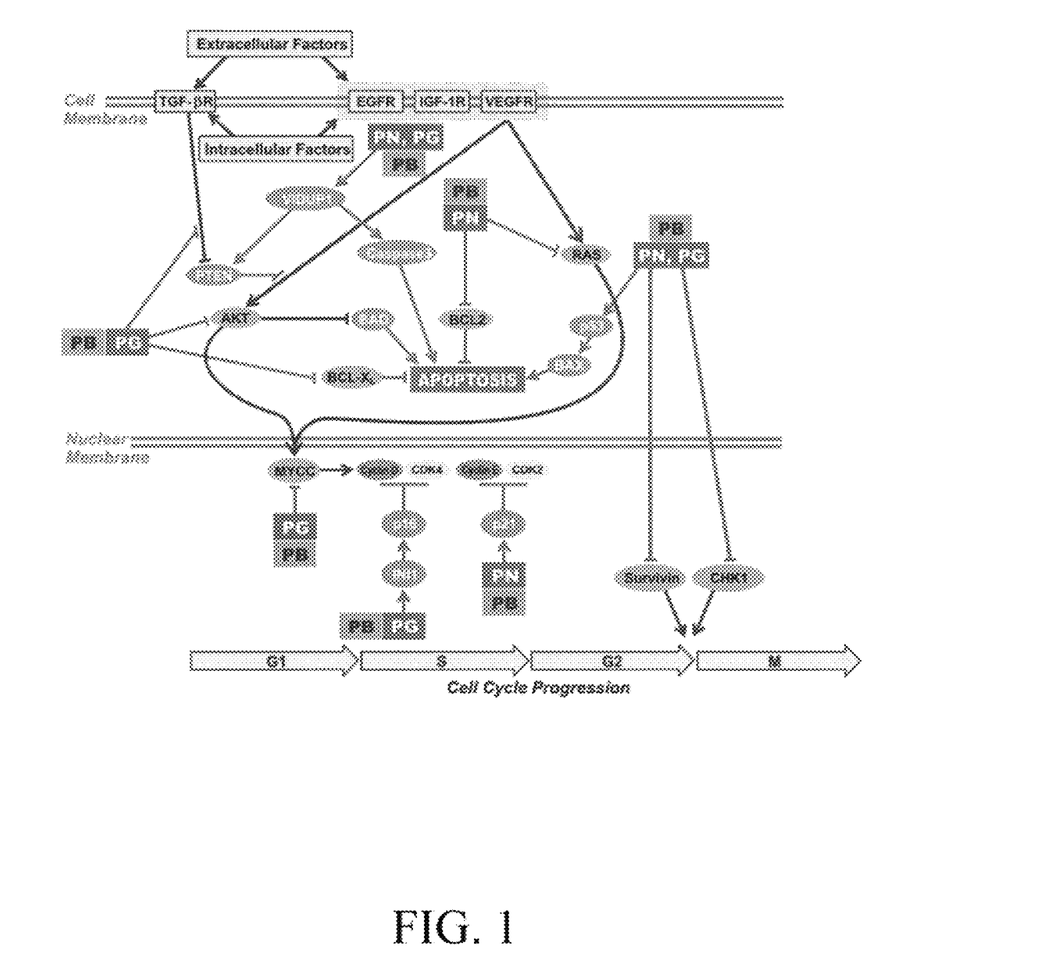
FIG. 1 is an illustration depicting a proposed mechanism of action of antineoplaston (ANP)/phenylbutyrate (PB) therapy in RGBM, according to an example embodiment of the present disclosure.
Figure 2:
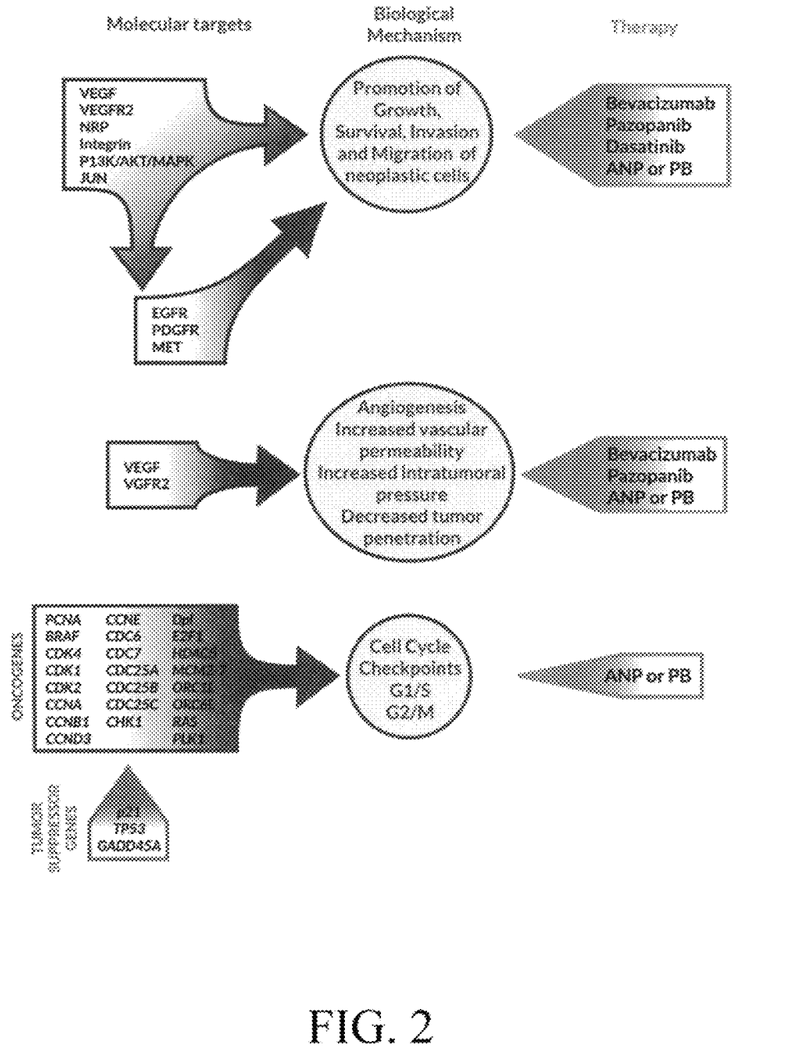
FIG. 2 is an illustration depicting the inhibition of growth, survival, invasion, angiogenesis, and cell cycle maintenance by ANP/PB therapy in combination with targeted agents, according to an example embodiment of the present disclosure.
Figure 3:
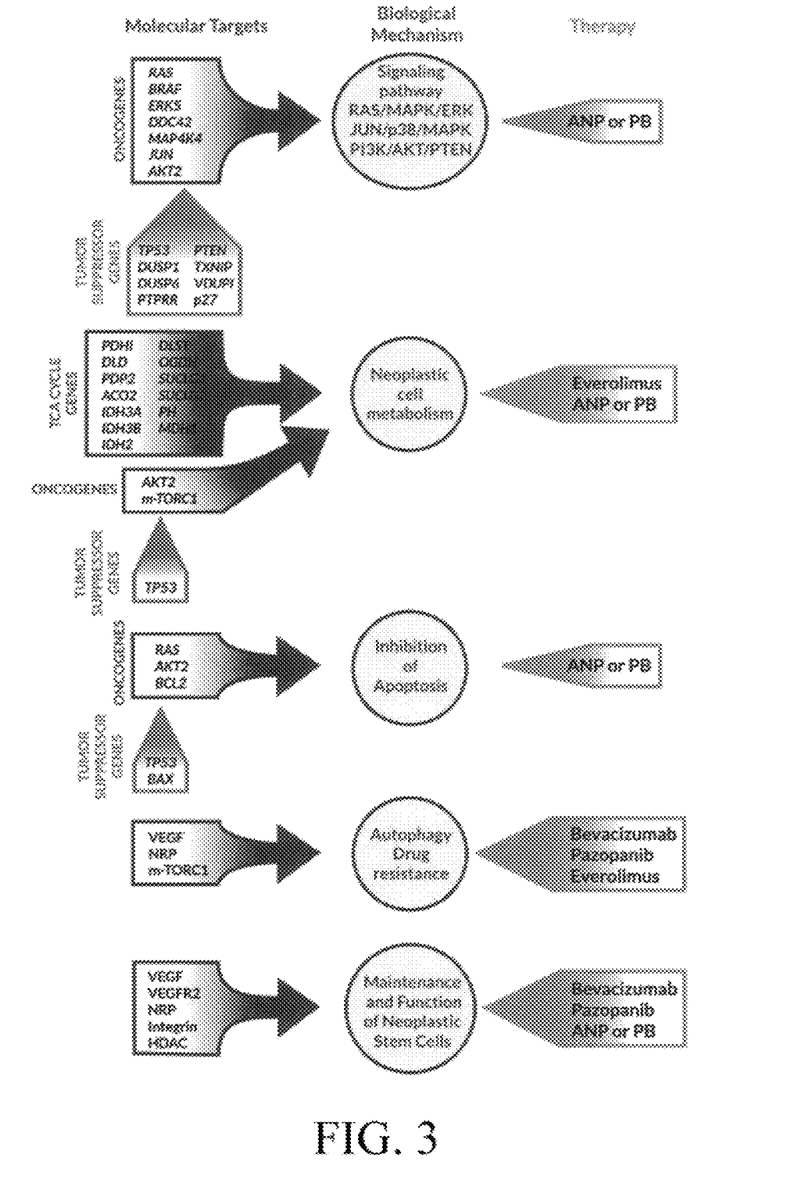
FIG. 3 is an illustration depicting the inhibition of signaling pathways, metabolism, drug resistance, and cell cycle maintenance and promotion of apoptosis by ANP/PB therapy in combination with targeted agents, according to an example embodiment of the present disclosure.

PB is a histone deacetylase inhibitor which is FDA-approved for urea cycle disorders. PB has also been used for the treatment of glioma and acute promyelocytic leukemia. The structural formula of PB is:

The metabolites of PB include PG and PN, the active ingredients in the ANP therapy and the ANP therapeutic composition. Without being held to any particular theory regarding the mechanism by which ANP and PB provides an effective therapeutic method of treating cancer, a proposed mechanism of action of ANP/PB therapy in RGBM is shown in FIG. 1. The inhibition of growth, survival, invasion, angiogenesis, and cell cycle maintenance by ANP/PB therapy in combination with targeted agents is shown in FIG. 2. The inhibition of signaling pathways, metabolism, drug resistance, and cell cycle maintenance and promotion of apoptosis by ANP/PB therapy in combination with targeted agents is shown in FIG. 3.

While the metabolites of PB include PG and PN, administration of PB may not be as effective as ANP therapy since PB relies on the generation of intermediates and products of metabolism, does not contain or produce iso-PG, and because PB is administered orally rather than intravenously.

The present disclosure provides combination therapeutic methods for the treatment of cancer in a patient. The method includes administering to a patient a plurality of extraneous antineoplastons and a plurality of targeted agents. In at least some instances, the plurality or antineoplastons and the plurality of targeted agents are administered to the patient concurrently. Concurrent administration of a plurality of extraneous antineoplastons and a plurality of targeted agents, according to the presently disclosed methods, have been discovered to be therapeutically effective in the treatment of cancer, in particular, in the treatment of gliomas including GMB and RGMB. Additionally, administration of a plurality of extraneous antineoplastons and a plurality of targeted agents, according to the presently disclosed dosage ranges and regimens, has been discovered to be therapeutically effective in the treatment of GMB and RGMB.

The plurality of targeted agents may include two or more agents selected from the group consisting of bevacizumab, pazopanib, sorafenib, dasatinib, and everolimus. Pazopanib and/or sorafenib may be orally administered to a patient at a dose of from about 1 mg/kg/day to about 12 mg/kg/day. In other cases, pazopanib and/or sorafenib may be orally administered to a patient at a dose of from about 2 mg/kg/day to about 6 mg/kg/day. In at least some instances, an optimal dose of pazopanib and/or sorafenib may be 3 mg/kg/day.

Dasatinib may be orally administered to a patient at a dose of from about 0.3 mg/kg/day to about 2.0 mg/kg/day. In other cases, dasatinib may be orally administered to a patient at a dose of from about 0.7 mg/kg/day to about 1.4 mg/kg/day. In at least some instances, an optimal dose of dasatinib may be 0.7 mg/kg/day.

Everolimus may be orally administered to a patient at a dose of from about 0.03 mg/kg/day to about 0.15 mg/kg/day. In other cases, everolimus may be orally administered to a patient at a dose of from about 0.03 mg/kg/day to about 0.10 mg/kg/day. In at least some instances, an optimal dose of everolimus may be 0.07 mg/kg/day.

Bevacizumab may be administered intravenously to a patient every 1 to 3 weeks at a dose of from about 2 mg/kg/day to about 15 mg/kg/day. In other cases, bevacizumab may be intravenously administered to a patient every 1 to 3 weeks at a dose of from about 5 mg/kg/day to about 12 mg/kg/day. In at least some instances, bevacizumab is optimally administered intravenously to a patient every 2 weeks and with an optimal dose of 10 mg/kg/day.

The plurality of extraneous antineoplastons may be administered intravenously to a patient. In some instances, the plurality of extraneous antineoplastons may include phenylacetylglutaminate sodium (PG) and phenylacetylisoglutaminate sodium (iso-PG). For example, the plurality of extraneous antineoplastons may be the Atengenal (A10) composition describe above. In such instances, the plurality of extraneous antineoplastons may include about a 4:1 ratio of PG and iso-PG. In at least some instances, the plurality of extraneous antineoplastons comprising PG and iso-PG may be administered intravenously to a patient at a dosage of from about 0.5 g/kg/day to about 25 g/kg/day. In other instances, the plurality of extraneous antineoplastons comprising PG and iso-PG may be administered intravenously to a patient at a dosage of from about 2 g/kg/day to about 8 g/kg/day. In at least some instances the optimal dose of extraneous antineoplastons comprising PG and iso-PG may be about 4 g/kg/day.

The plurality of extraneous antineoplastons may be administered intravenously to a patient at a dosage of from about 0.4 g/kg/day to about 20 g/kg/day phenylacetylglutaminate sodium (PG) and from about 0.1 g/kg/day to about 5 g/kg/day phenylacetylisoglutaminate sodium (iso-PG). In other instances, the plurality of extraneous antineoplastons may be administered intravenously to a patient at a dosage of from about 1.6 g/kg/day to about 6.4 g/kg/day phenylacetylglutaminate sodium (PG) and from about 0.4 g/kg/day to about 1.6 g/kg/day phenylacetylisoglutaminate sodium (iso-PG). In at least some instances, the optimal dose of phenylacetylglutaminate sodium (PG) may be 3.2 g/kg/day and the optimal dose of phenylacetylisoglutaminate sodium (iso-PG) may be 0.8 g/kg/day.

In some instances, the plurality of extraneous antineoplastons may include phenylacetate (PN) and phenylacetylglutaminate (PG). For example, the plurality of extraneous antineoplastons may be the Astugenal (AS2-1) composition described above. In such instances, the plurality of extraneous antineoplastons may include about a 4:1 ratio of PN and PG. In at least some instances, the plurality of extraneous antineoplastons comprising PN and PG may be administered intravenously to a patient at a dosage of from about 0.04 g/kg/day to about 0.6 g/kg/day. In other instances, the plurality of extraneous antineoplastons comprising PN and PG may be administered intravenously to a patient at a dosage of from about 0.2 g/kg/day to about 0.4 g/kg/day. In at least some instances the optimal dose of extraneous antineoplastons comprising PN and PG may be about 0.4 g/kg/day.

The plurality of extraneous antineoplastons may be administered intravenously to a patient at a dosage of from about 0.064 g/kg/day to about 0.48 g/kg/day phenylacetate (PN) and from about 0.016 g/kg/day to about 0.12 g/kg/day phenylacetylglutaminate sodium (PG). In other instances, the plurality of extraneous antineoplastons may be administered intravenously to a patient at a dosage of from about 0.16 g/kg/day to about 0.48 g/kg/day phenylacetate (PN) and from about 0.04 g/kg/day to about 0.12 g/kg/day phenylacetylglutaminate sodium (PG). In at least some instances, the optimal dose of phenylacetate (PN) may be 0.32 g/kg/day and the optimal dose of phenylacetylglutaminate sodium (PG) may be 0.08 g/kg/day.

In at least some instances, the plurality of extraneous antineoplastons may include phenylacetylglutaminate sodium (PG), phenylacetylisoglutaminate sodium (iso-PG), phenylacetate (PN), and any combination thereof.

The plurality of extraneous antineoplastons and the pazopanib, sorafenib, dasatinib, and everolimus may be administered daily for one to seven days. In some instances, the plurality of extraneous antineoplastons and the pazopanib, sorafenib, dasatinib, and everolimus may be administered daily for at least 8 weeks and the bevacizumab may be administered intravenously every 1 to 3 weeks for at least 8 weeks.

In at least some instances, the concurrent administration of the plurality of extraneous antineoplastons and the plurality of targeted agents may begin on different days at the beginning of the treatment regimen in order to better monitor the onset of adverse events. For example, the ANP therapy may begin on day 1 and continue daily for the duration of the treatment regimen. On day 2, one of the plurality of targeted agents may be orally administered and continued daily for the duration of the treatment regimen. On day 3, a second one of the plurality of targeted agents may be orally administered and continued daily for the duration of the treatment regimen. A third and fourth targeted agents may be orally administered on day 3 and day 4, respectively, and continued daily for the duration of the treatment regimen. Intravenous administration of bevacizumab may begin on day 5 of the treatment regimen and repeated once every 1-3 weeks thereafter for so long as the treatment regimen continues. No rest period is required for the any of the administered therapeutic compositions. The treatment regimen may continue, for example, for 8 weeks. An MRI scan may then be used to determine if an objective response has occurred. The treatment regimen may then be repeated as needed, with or without the staggered onset of concurrent administration.

In other instances, the ANP therapy may begin on day 1 with escalating dosages administered on days 2-4. ANP therapy may then continue daily for the duration of the treatment regimen. Intravenous administration of bevacizumab may begin on day 8 of the treatment regimen and repeated once every 1-3 weeks thereafter for so long as the treatment regimen continues. Dasatinib may be administered on day 12 and continued daily for the duration of the treatment regimen. Everolimus may be administered on day 16 and continued daily for the duration of the treatment regimen. Pazopanib may be administered on day 20 and continued daily for the duration of the treatment regimen. The treatment regimen may continue, for example, for 8 weeks. An MRI scan may then be used to determine if an objective response has occurred. The treatment regimen may then be repeated as needed, with or without the staggered onset of concurrent administration.

According to at least one aspect of the present disclosure, the antineoplaston (ANP) therapy may be administered to a patient in combination with sodium phenylbutyrate (PB). In some instances, the ANP therapy and/or the intravenous administration of the plurality of antineoplastons may be replaced by administration of PB.

EXAMPLES

Example 1: A 47 year-old male patient from Australia had undergone subtotal resection of a right parieto-occipital GBM followed by treatment with temozolomide (TMZ) and concomitant radiation therapy. A post-treatment MRI indicated RGBM. The patient began ANP therapy in combination with a plurality of targeted agents. The patient was intravenously administered an ANP therapeutic composition comprising 6.3 g/kg/day of A10 and 0.2 g/kg/day AS2-1 for approximately 8 months. Concurrently, the patient received oral administration of dasatinib (0.5 mg/kg/day), everolimus (0.1 mg/kg/day), and pazopanib (2.1 mg/kg/day) at doses representing a 50-80% dose reduction as compared to the standard dose. The patient concurrently received intravenous administration of bevacizumab (7.5 mg/kg) every two weeks. After approximately 26 days of treatment, an MRI revealed no measureable enhancing disease. A subsequent MRI after 54 days of treatment indicated a disappearance of all enhancing disease. After approximately 84 days of treatment, a PET/CT scan revealed no metabolically active disease. The patient returned to Australia after 55 days. The patient's current condition is not known.

Example 2: A male patient from Australia had undergone resection of a GBM, which involved his right temporal, parietal, and occipital lobes and the corpus callosum, followed by treatment with temozolomide (TMZ) and concomitant radiation therapy. Two weeks after completion of that therapy, the patient underwent a second surgical resection for RGBM. Subsequently, a MRI revealed a 5.2 cm×4.3 cm tumor. Assisted by molecular profiling, the patient was administered PB, bevacizumab, erlotinib, rapamycin, and TMZ. After six weeks of treatment there was no evidence of tumor on a repeat MRI scan. The patient remained free of disease for over three years when a MRI revealed RGBM. The patient underwent resection of the RGBM, however, approximately one month later, a MRI revealed a 4.8 $cm^2$ right temporal enhancing mass.

At the age of 57, the patient began ANP therapy in combination with a plurality of targeted agents. The patient was intravenously administered an ANP therapeutic composition comprising 6.6 g/kg/day of A10 and 0.2 g/kg/day of AS2-1 for 67 days. Concurrently, the patient received oral administration of dasatinib (0.5 mg/kg/day), everolimus (0.05 mg/kg/day), and pazopanib (2.2 mg/kg/day) at doses representing a 50-80% dose reduction as compared to the standard dose. The patient concurrently received intravenous administration of bevacizumab (10 mg/kg) every two weeks. After approximately 74 days of treatment, a MRI performed on the patient revealed no measureable enhancing disease. A subsequent PET/CT scan after 105 days from the start of treatment revealed no metabolically active disease. The patient returned to Australia where is oncologist discontinued treatment. He died approximately one year from treatment start.

Example 3: A 23 year-old female patient had been diagnosed with fibrillary astrocytoma, grade II, IDH1(−). The patient underwent resection of the tumor but developed tumor recurrence within approximately one year, as indicated by an MRI. Further progression was shown by an MRI performed approximately one month later. The patient underwent a second tumor resection approximately two months later and the pathology showed a glioblastoma, unmethylated MGMT, wild type IDH1 and BRAF mutation. The patient received adjuvant radiation therapy for approximately 42 days. Fourteen days later, the patient received oral administration of PB (0.2 g/kg/day), sorafenib (3.6 mg/kg/day), everolimus (0.09 mg/kg/day), dasatinib (0.9 mg/kg/day), concurrent with intravenous administration of bevacizumab (10 mg/kg) every two weeks. A pretreatment MRI revealed a contrast-enhancing lesion measuring 2.5 cm×2.0 cm. A follow-up MRI approximately 3 months after treatment began indicated no recurrent tumor and a subsequent MRI approximately 46 days later confirmed a complete response. Two days later, ANP therapy comprising intravenous administration of AS2-1 through a portable infusion pump were concurrently added to the treatment of the patient. The dose of the AS2-1 ANP therapy was gradually increased to 40 mL (80 mg/mL) six times daily at 250 mL/hour (0.34 g/kg/day). A follow-up MRI approximately 3 months later indicated continuation of the complete response. The patient continued the treatment for 8 months. Currently, she is off treatment for 5 months and continues to be tumor-free.

Example 4: A 71 year-old female patient with a history of hypothyroidism and diabetes was in her usual state of health until she began having visual impairment. An MRI revealed a large 6 cm×3 cm brain tumor in the left occipital region. The patient received resection and the pathology was consistent with glioblastoma. Because of her poor prognosis, the patient refused radiation therapy or cytotoxic chemotherapy. The patient began ANP therapy in combination with a plurality of targeted agents. The ANP therapy comprised intravenous administration of AS2-1 through a subclavian vein catheter and portable infusion pump. The dose of the AS2-1 ANP therapy was gradually increased to 40 mL (80 mg/mL) six times daily at 250 mL/hour (0.34 g/kg/day). Concurrently, the patient received daily oral administration of dasatinib (0.7 mg/kg/day), everolimus (0.07 mg/kg/day), and pazopanib (3.2 mg/kg/day). The patient also concurrently received intravenous administration of bevacizumab (10 mg/kg) every two weeks. A baseline MRI prior to ANP therapy revealed a contrast-enhancing nodule at the margin of the postoperative cavity measuring 1.0 cm×0.6 cm. A follow-up MRI after approximately 40 days of treatment indicated the resolution of the nodule. A subsequent MRI after approximately 75 days of treatment confirmed a complete response and indicated a decrease in the postoperative cavity from 3.6 cm×3.1 cm to 2.0 cm×2.8 cm. The patient experienced numerous interruptions of the treatment due to soreness in the mouth. As a result, the tumor relapsed after 103 days and the patient died four months later.

Statements of the Disclosure Include:

Statement 1: A method for treating cancer in a patient in need thereof, the method comprising administering to a patient: (a) a plurality of extraneous antineoplastons; and (b) a plurality of targeted agents, wherein the plurality of targeted agents comprises two or more agents selected from the group consisting of bevacizumab, pazopanib, sorafenib, dasatinib, and everolimus.

Statement 2: A method according to Statement 1, wherein the plurality of extraneous antineoplastons comprises phenylacetylglutaminate sodium (PG) and phenylacetylisoglutaminate sodium (iso-PG).

Statement 3: A method according to Statement 1 or Statement 2, wherein the plurality of extraneous antineoplastons comprises about a 4:1 ratio of synthetic phenylacetylglutaminate sodium (PG) and synthetic phenylacetylisoglutaminate sodium (iso-PG).

Statement 4: A method according to Statement 2 or Statement 3, comprising intravenous administration of the plurality of extraneous antineoplastons to the patient at a dosage of from about 0.5 g/kg/day to about 20 g/kg/day.

Statement 5: A method according to Statement 2 or Statement 3, comprising intravenous administration of the plurality of extraneous antineoplastons to the patient at a dosage of from about 2 g/kg/day to about 8 g/kg/day.

Statement 6: A method according to any one of the preceding Statements 1-3, comprising intravenous administration of the plurality of extraneous antineoplastons in the following amounts: from about 0.4 g/kg/day to about 16 g/kg/day phenylacetylglutaminate sodium (PG); and from about 0.1 g/kg/day to about 4 g/kg/day phenylacetylisoglutaminate sodium (iso-PG).

Statement 7: A method according to any one of the preceding Statements 1-3, comprising intravenous administration of the plurality of extraneous antineoplastons in the following amounts: from about 1.6 g/kg/day to about 6.4 g/kg/day phenylacetylglutaminate sodium (PG); and from about 0.4 g/kg/day to about 1.6 g/kg/day phenylacetylisoglutaminate sodium (iso-PG).

Statement 8: A method according to Statement 1, wherein the plurality of extraneous antineoplastons comprises phenylacetate (PN) and phenylacetylglutaminate (PG).

Statement 9: A method according to Statement 1 or Statement 8, wherein plurality of extraneous antineoplastons comprises about a 4:1 ratio of phenylacetate (PN) and phenylacetylglutaminate (PG).

Statement 10: A method according to Statement 8 or Statement 9, comprising intravenous administration of the plurality of extraneous antineoplastons to the patient at a dosage of from about 0.08 g/kg/day to about 0.6 g/kg/day.

Statement 11: A method according to Statement 8 or Statement 9, comprising intravenous administration of the plurality of extraneous antineoplastons to the patient at a dosage of from about 0.2 g/kg/day to about 0.6 g/kg/day.

Statement 12: A method according to Statement 8 or Statement 9, comprising intravenous administration of the plurality of extraneous antineoplastons in the following amounts: from about 0.064 g/kg/day to about 0.48 g/kg/day phenylacetate (PN); and from about 0.016 g/kg/day to about 0.12 g/kg/day phenylacetylglutaminate sodium (PG).

Statement 13: A method according to Statement 8 or Statement 9, comprising intravenous administration of the plurality of extraneous antineoplastons in the following amounts: from about 0.16 g/kg/day to about 0.48 g/kg/day phenylacetate (PN); and from about 0.04 g/kg/day to about 0.12 g/kg/day phenylacetylglutaminate sodium (PG).

Statement 14: A method according to any one of the preceding Statements 1-13, wherein the plurality of extraneous antineoplastons comprises phenylacetylglutaminate sodium (PG), phenylacetylisoglutaminate sodium (iso-PG), and phenylacetate (PN).

Statement 15: A method according to any one of the preceding Statements 1-14, wherein the plurality of extraneous antineoplastons is administered intravenously.

Statement 16: A method according to any one of the preceding Statements 1-15, wherein administration of the plurality of targeted agents comprises oral administration of two or more of pazopanib, sorafenib, dasatinib, and everolimus and intravenous administration of bevacizumab.

Statement 17: A method according to any one of the preceding Statements 1-16, wherein the plurality of targeted agents are administered according to the following dosages: pazopanib and sorafenib is administered orally at a dose of from about 1 mg/kg/day to about 12 mg/kg/day; dasatinib is administered orally at a dose of from about 0.3 mg/kg/day to about 2.0 mg/kg/day; everolimus is administered orally at a dose of from about 0.03 mg/kg/day to about 0.15 mg/kg/day; and bevacizumab is administered intravenously every 1 to 3 weeks at a dose of from about 2 mg/kg/day to about 15 mg/kg/day.

Statement 18: A method according to any one of the preceding Statements 1-16, wherein the plurality of targeted agents are administered according to the following dosages: pazopanib and sorafenib is administered orally at a dose of from about 2 mg/kg/day to about 6 mg/kg/day; dasatinib is administered orally at a dose of from about 0.7 mg/kg/day to about 1.4 mg/kg/day; everolimus is administered orally at a dose of from about 0.03 mg/kg/day to about 0.10 mg/kg/day; and bevacizumab is administered intravenously every 1 to 3 weeks at a dose of from about 5 mg/kg/day to about 12 mg/kg/day.

Statement 19: A method according to any one of the preceding Statements 1-18, wherein the plurality of extraneous antineoplastons and the pazopanib, sorafenib, dasatinib, and everolimus are administered daily for one to seven days.

Statement 20: A method according to any one of the preceding Statements 1-18, wherein the plurality of extraneous antineoplastons and the pazopanib, sorafenib, dasatinib, and everolimus are administered daily for at least 8 weeks and the bevacizumab is administered intravenously every 1 to 3 weeks for at least 8 weeks.

Statement 21: A method according to any one of the preceding Statements 1-20, wherein the cancer is a glioma.

Statement 22: A method according to any one of the preceding Statements 1-21, wherein the cancer is glioblastoma multiforme (GBM) or recurrent glioblastoma multiforme (RGBM).

Statement 23: A method according to any one of the preceding Statements 1-22, further comprising genomic profiling of a tumor in the patient to determine the genetic subtype.

Statement 24: A method according to any one of the preceding Statements 1-23, wherein the GBM or RGBM is of the Classical subtype or the Proneural subtype.

Statement 25: A method according to any one of the preceding Statements 1-24, wherein the patient has failed to achieve an objective response as a result of radiation treatment and/or chemotherapy treatment, prior to the administration of the plurality of extraneous antineoplastons and the plurality of targeted agents.

Statement 26: A method according to any one of the preceding Statements 1-25, wherein the patient has failed to achieve an objective response as a result of chemotherapy treatments comprising temozolomide (TMZ) and/or bevacizumab (BVZ), prior to the administration of the plurality of extraneous antineoplastons and the plurality of targeted agents.

Statement 27: A method according to any one of the preceding Statements 1-26, wherein the patient has undergone a resection of a glioma prior to the administration of the plurality of extraneous antineoplastons and the plurality of targeted agents.

Statement 28: A method for treating cancer in a patient in need thereof, the method comprising concurrently administering to a patient: (a) a plurality of extraneous antineoplastons; (b) a plurality of targeted agents, the plurality of targeted agents comprising two or more agents selected from the group consisting of pazopanib, sorafenib, dasatinib, and everolimus; and (c) bevacizumab.

Statement 29: A method according to Statement 28, wherein the plurality of targeted agents are administered according to the following dosages: pazopanib and sorafenib is administered orally at a dose of from about 1 mg/kg/day to about 12 mg/kg/day; dasatinib is administered orally at a dose of from about 0.3 mg/kg/day to about 2.0 mg/kg/day; everolimus is administered orally at a dose of from about 0.03 mg/kg/day to about 0.15 mg/kg/day; and bevacizumab is administered intravenously every 1 to 3 weeks at a dose of from about 2 mg/kg/day to about 15 mg/kg/day.

Statement 30: A method according to Statement 28, wherein the plurality of targeted agents are administered according to the following dosages: pazopanib and sorafenib is administered orally at a dose of from about 2 mg/kg/day to about 6 mg/kg/day; dasatinib is administered orally at a dose of from about 0.7 mg/kg/day to about 1.4 mg/kg/day; everolimus is administered orally at a dose of from about 0.03 mg/kg/day to about 0.10 mg/kg/day; and bevacizumab is administered intravenously every 1 to 3 weeks at a dose of from about 5 mg/kg/day to about 12 mg/kg/day.

Statement 31: A method according to any one of the preceding Statements 28-30, wherein the plurality of extraneous antineoplastons and the pazopanib, sorafenib, dasatinib, and everolimus are administered daily for one to seven days.

Statement 32: A method according to any one of the preceding Statements 28-30, wherein the plurality of extraneous antineoplastons and the pazopanib, sorafenib, dasatinib, and everolimus are administered daily for at least 8 weeks and the bevacizumab is administered intravenously every 1 to 3 weeks for at least 8 weeks.

Statement 33: A method according to any one of the preceding Statements 28-32, wherein the plurality of extraneous antineoplastons comprises phenylacetylglutaminate sodium (PG) and phenylacetylisoglutaminate sodium (iso-PG).

Statement 34: A method according to any one of the preceding Statements 28-33, wherein the plurality of extraneous antineoplastons comprises about a 4:1 ratio of synthetic phenylacetylglutaminate sodium (PG) and synthetic phenylacetylisoglutaminate sodium (iso-PG).

Statement 35: A method according to Statement 33 or Statement 34, comprising intravenous administration of the plurality of extraneous antineoplastons to the patient at a dosage of from about 0.5 g/kg/day to about 20 g/kg/day.

Statement 36: A method according to Statement 33 or Statement 34, comprising intravenous administration of the plurality of extraneous antineoplastons to the patient at a dosage of from about 2 g/kg/day to about 8 g/kg/day.

Statement 37: A method according to Statement 33 or Statement 34, comprising intravenous administration of the plurality of extraneous antineoplastons in the following amounts: from about 0.4 g/kg/day to about 16 g/kg/day phenylacetylglutaminate sodium (PG); and from about 0.1 g/kg/day to about 4 g/kg/day phenylacetylisoglutaminate sodium (iso-PG).

Statement 38: A method according to Statement 33 or Statement 34, comprising intravenous administration of the plurality of extraneous antineoplastons in the following amounts: from about 1.6 g/kg/day to about 6.4 g/kg/day phenylacetylglutaminate sodium (PG); and from about 0.4 g/kg/day to about 1.6 g/kg/day phenylacetylisoglutaminate sodium (iso-PG).

Statement 39: A method according to any one of the preceding Statements 28-32, wherein the plurality of extraneous antineoplastons comprises phenylacetate (PN) and phenylacetylglutaminate (PG).

Statement 40: A method according to Statement 39, wherein plurality of extraneous antineoplastons comprises about a 4:1 ratio of phenylacetate (PN) and phenylacetylglutaminate (PG).

Statement 41: A method according to Statement 39 or Statement 40, comprising intravenous administration of the plurality of extraneous antineoplastons to the patient at a dosage of from about 0.08 g/kg/day to about 0.6 g/kg/day.

Statement 42: A method according to Statement 39 or Statement 40, comprising intravenous administration of the plurality of extraneous antineoplastons to the patient at a dosage of from about 0.2 g/kg/day to about 0.6 g/kg/day.

Statement 43: A method according to Statement 39 or Statement 40, comprising intravenous administration of the plurality of extraneous antineoplastons in the following amounts: from about 0.064 g/kg/day to about 0.48 g/kg/day phenylacetate (PN); and from about 0.016 g/kg/day to about 0.12 g/kg/day phenylacetylglutaminate sodium (PG).

Statement 44: A method according to Statement 39 or Statement 40, comprising intravenous administration of the plurality of extraneous antineoplastons in the following amounts: from about 0.16 g/kg/day to about 0.48 g/kg/day phenylacetate (PN); and from about 0.04 g/kg/day to about 0.12 g/kg/day phenylacetylglutaminate sodium (PG).

Statement 45: A method according to any one of the preceding Statements 28-32, wherein the plurality of extraneous antineoplastons comprises phenylacetylglutaminate sodium (PG), phenylacetylisoglutaminate sodium (iso-PG), and phenylacetate (PN).

What is claimed is:

1. A method for treating glioblastoma multiforme (GBM) or recurrent glioblastoma multiform (RGBM) in a patient in need thereof, the method comprising:
   administering to a patient having glioblastoma multiforme (GBM) or recurrent glioblastoma multiform (RGBM):
      (a) a plurality of extraneous antineoplastons
         wherein the plurality of extraneous antineoplastons comprises AS2-1 and/or A10,
            wherein AS2-1 comprises from about 0.064 g/kg/day to about 0.48 g/kg/day phenylacetate (PN) and from about 0.016 g/kg/day to about 0.12 g/kg/day phenylacetylglutaminate sodium (PG) in a 4:1 ratio,
            wherein A10 comprises from about 0.4 g/kg/day to about 20 g/kg/day phenylacetylglutaminate sodium (PG) and from about 0.1 g/kg/day to about 5 g/kg/day phenylacetylisoglutaminate sodium (iso-PG) in a 4:1 ratio; and
      (b) a plurality of targeted agents, wherein the plurality of targeted agents comprises
         from about 2 mg/kg/day to about 15 mg/kg/day bevacizumab,
         from about 1 mg/kg/day to about 12 mg/kg/day pazopanib and/or sorafenib,
         from about 0.3 mg/kg/day to about 2.0 mg/kg/day dasatinib, and
         from about 0.03 mg/kg/day to about 0.15 mg/kg/day everolimus,
      wherein an objective response is obtained.

2. The method of claim 1, wherein the patient previously failed to achieve an objective response following at least one radiation treatment and/or at least chemotherapy treatment comprising temozolomide (TMZ) and/or bevacizumab (BVZ).

3. The method of claim 1, wherein the plurality of extraneous antineoplastons and the plurality of targeted agents are administered as part of a treatment regimen comprising at least 8 weeks.

4. The method of claim 1, wherein the plurality of extraneous antineoplastons are administered with escalating dosages.

5. The method of claim 1, further comprising orally administering to the patient sodium phenylbutyrate (PB).

6. The method of claim 1, wherein administering pazopanib and/or sorafenib, dasatinib, and everolimus comprises oral administration, and wherein administering bevacizumab comprises intravenous administration.

7. The method of claim 1, wherein the GBM or RGBM is determined to be of the Classical subtype or the Proneural subtype by genomic profiling.

8. The method of claim 3, wherein AS2-1 and/or A10, pazopanib and/or sorafenib, dasatinib, and everolimus are administered daily for the at least 8 weeks of the treatment regimen, and bevacizumab is administered every 1 to 3 weeks for the at least 8 weeks of the treatment regimen.

9. The method of claim 1, wherein a magnetic resonance imaging (MRI) is used to determine whether an objective response is obtained.

10. The method of claim 1, wherein prior to the administering step, the patient underwent a resection of a glioma.

11. A method of treating glioblastoma multiforme (GBM) or recurrent glioblastoma multiforme (RGBM) in a patient in need thereof, the method comprising:
   administering to a patient having GBM or RGBM an 8-week treatment regimen,
      wherein the treatment regimen comprises a plurality of extraneous antineoplastons and a plurality of targeted agents,
      wherein the plurality of extraneous antineoplastons comprises
         (i) AS2-1 comprising from about 0.064 g/kg/day to about 0.48 g/kg/day phenylacetate (PN) and from about 0.016 g/kg/day to about 0.12 g/kg/day phenylacetylglutaminate sodium (PG) in a 4:1 ratio, and
         (ii) A10 comprising from about 0.4 g/kg/day to about 20 g/kg/day phenylacetylglutaminate sodium (PG) and from about 0.1 g/kg/day to about 5 g/kg/day phenylacetylisoglutaminate sodium (iso-PG) in a 4:1 ratio; and wherein administration of the extraneous antineoplastons begins on day 1 of the treatment regimen and continues daily;

wherein the plurality of targeted agents comprises from about 1 mg/kg/day to about 12 mg/kg/day pazopanib, from about 1 mg/kg/day to about 12 mg/kg/day sorafenib, from about 0.3 mg/kg/day to about 2.0 mg/kg/day dasatinib, from about 0.03 mg/kg/day to about 0.15 mg/kg/day everolimus, and from about 2 mg/kg/day to about 15 mg/kg/day bevacizumab;

wherein administration of the first targeted agent begins on day 2 of treatment regimen and continues daily;

wherein administration of the second targeted agent begins on day 3 of the treatment regimen and continues daily;

wherein administration of the third targeted agent begins on day 3 of the treatment regimen and continues daily;

wherein administration of the fourth target agent beings on day 4 of the treatment regimen and continues daily; and wherein administration of bevacizumab begins on day 5 of the treatment regimen and continues every 1 to 3 weeks.

12. The method of claim 11, wherein the patient previously failed to achieve an objective response following at least one radiation treatment and/or at least chemotherapy treatment comprising temozolomide and/or bevacizumab.

13. The method of claim 11, wherein a magnetic resonance (MRI) is used to determine whether an objective response is obtained.

* * * * *